US008830233B2

(12) United States Patent
Friedland et al.

(10) Patent No.: US 8,830,233 B2
(45) Date of Patent: Sep. 9, 2014

(54) SURGICAL CASE PLANNING PLATFORM

(75) Inventors: Richard Friedland, Suffern, NY (US);
Robert Campomenosi, Wayne, NJ (US);
Justin Anthony Corona, Park Ridge, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 161 days.

(21) Appl. No.: 13/449,462

(22) Filed: Apr. 18, 2012

(65) Prior Publication Data
US 2012/0274631 A1 Nov. 1, 2012

Related U.S. Application Data

(60) Provisional application No. 61/479,950, filed on Apr. 28, 2011.

(51) Int. Cl.
| G06T 15/00 | (2011.01) |
| G06T 15/10 | (2011.01) |
| G06T 15/20 | (2011.01) |
| A61B 19/00 | (2006.01) |
| G06F 19/00 | (2011.01) |
| G06T 19/20 | (2011.01) |

(52) U.S. Cl.
CPC ............. *A61B 19/50* (2013.01); *G06T 2210/41* (2013.01); *G06F 19/3437* (2013.01); *G06T 19/20* (2013.01); *A61B 2019/505* (2013.01); *G06F 19/3481* (2013.01); *G06T 2219/2004* (2013.01); *A61B 2019/502* (2013.01); *A61B 2019/508* (2013.01); *Y10S 128/92* (2013.01); *Y10S 128/922* (2013.01)
USPC ............................ 345/419; 128/920; 128/922

(58) Field of Classification Search
CPC ..... G06T 15/00; G06T 19/00; G06T 2200/08; G06T 2201/00; G06T 2200/04; G06F 19/00; G06Q 50/20; G06Q 50/22
See application file for complete search history.

(56) References Cited

U.S. PATENT DOCUMENTS

| 5,513,101 A | 4/1996 | Pinsky et al. |
| 5,740,428 A | 4/1998 | Mortimore et al. |

(Continued)

FOREIGN PATENT DOCUMENTS

| EP | 0429148 A1 | 5/1991 |
| EP | 0469966 A1 | 2/1992 |

OTHER PUBLICATIONS

First Stryker iPad Apps for Surgeons Now Available on the App Store, Stryker Orthopaedics Kwittken & Company, Feb. 17, 2011.
Gao et al., A Survey of 3D Head Modeal Retrieval, Second International Conference on Intelligent Computation Technology and Automation, 515-519, 2009.

(Continued)

*Primary Examiner* — Kee M Tung
*Assistant Examiner* — Wei Yuan
(74) *Attorney, Agent, or Firm* — Lerner, David, Littenberg, Krumholz & Mentlik, LLP

(57) ABSTRACT

Computer-implemented systems and methods of preoperatively planning a present surgical case including a surgical site located on a portion of a body of a patient are described herein. Such methods may include converting at least one image of the surgical site into a three-dimensional model displayable on a display means and manipulating the model such that the model is displayable on the display means as a corrected model representing a corrected surgical site. The method may further include providing at least one medical device from a library of medical devices stored in a device database and providing a plurality of previous surgical cases maintained in a case database the plurality of previous surgical cases being made available for preoperatively planning the present surgical case.

12 Claims, 12 Drawing Sheets

(56) References Cited

U.S. PATENT DOCUMENTS

| | | | |
|---|---|---|---|
| 5,920,317 | A | 7/1999 | McDonald |
| 6,381,029 | B1 | 4/2002 | Tipirneni |
| 6,798,533 | B2 | 9/2004 | Tipirneni |
| 6,901,277 | B2 | 5/2005 | Kaufman et al. |
| 7,106,479 | B2 | 9/2006 | Roy et al. |
| 7,180,624 | B2 | 2/2007 | Tipirneni |
| 7,251,374 | B2 | 7/2007 | Niemeyer |
| 7,756,724 | B2 | 7/2010 | Gropper et al. |
| 7,885,441 | B2 | 2/2011 | Node-Langlois et al. |
| 2004/0068187 | A1* | 4/2004 | Krause et al. ............ 600/443 |
| 2005/0096530 | A1 | 5/2005 | Daw et al. |
| 2005/0113651 | A1 | 5/2005 | Wood et al. |
| 2006/0155577 | A1 | 7/2006 | Niemeyer |
| 2008/0130970 | A1 | 6/2008 | Niemeyer et al. |
| 2009/0149977 | A1 | 6/2009 | Schendel |
| 2009/0172773 | A1 | 7/2009 | Moore |
| 2009/0204683 | A1 | 8/2009 | Tipirneni |
| 2010/0191244 | A1 | 7/2010 | White et al. |
| 2010/0329530 | A1 | 12/2010 | Lang et al. |
| 2011/0029093 | A1 | 2/2011 | Bojarski et al. |

OTHER PUBLICATIONS

InVivoLink releases iPad app for analyzing orthopedic practice patterns, ORTHOSuperSite, Apr. 6, 2011.

Iserhardt-Bauer et al., Case Study: Medical Web Service for the Automatic 3D Documentation for Neuroradiological Diagnosis, Presented at IEEE Visualization, San Diego, Oct. 21-Oct. 26, 2001.

Liu et al., Content-based 3D Neuroradiologic Image Retrieval: Preliminary Results, IEEE, 91-100, 1997.

Liu et al., Robust Midsagittal Plane Extraction form Normal and Pathological 3-D Neuroradiology Images, IEEE Transactions on Medical Imaging, vol. 20, No. 3, Mar. 2001.

Lumbar Body Fusion Changes The Life Of Young Girl, New Jersey Spine and Rehabilitation <http://www.njsrlaserspine.com>, Apr. 6, 2011.

Orthopaedic Surgeons Launch National Campaign to Stop Distracted Driving, PRNewswire—USNewswire, Washington, Apr. 6, 2011.

OsiriX Imaging Software, Advanced Open-Source PACS Workstation DICOM Viewer, printed Mar. 30, 2011.

Patients with less preoperative motion may benefit more from high-flexion knees, Posted on the ORTHOSuperSite, Apr. 6, 2011.

Pre-operative planning and understanding implant utilization are key to a successful total joint program, InVivoLink, 2010.

Rowe et al., Acquisition, Representation, Query and Analysis of Spatial Data: A Demonstration 3D Digital Library, Proceedings of the 2003 Joint Conference on Digital Libraries, 2003.

Sarni et al., A Spreadsheet Framework for Visual Exploration of Biomedical Datasets, Proceedings of the 18th IEEE Symposium on Computer-Based Medical Systems, 2005.

Schimpff et al., Operating Room of the Future, Final Proceedings, University of MD Medical Center and US Army Medical Research and Materiel Command, Jan. 2003.

Tsai et al., Volume Manipulations for Simulating Bone and Joint Surgery, IEE Transactions on Information Technology in Biomedicine, vol. 9, No. 1, 139-149, Mar. 2005.

Wong et al., A Digital Library for Biomedical Imaging on the Internet, IEEE Communications Magazine, 84-91, Jan. 1999.

Xie et al., 3D Voxel Fusion of Multi-Mordality Medical Images in a Clinical Treatment Planning System, Proceedings of the 17th IEEE Symposium on Computer-Based Medical Systems, 2004.

* cited by examiner

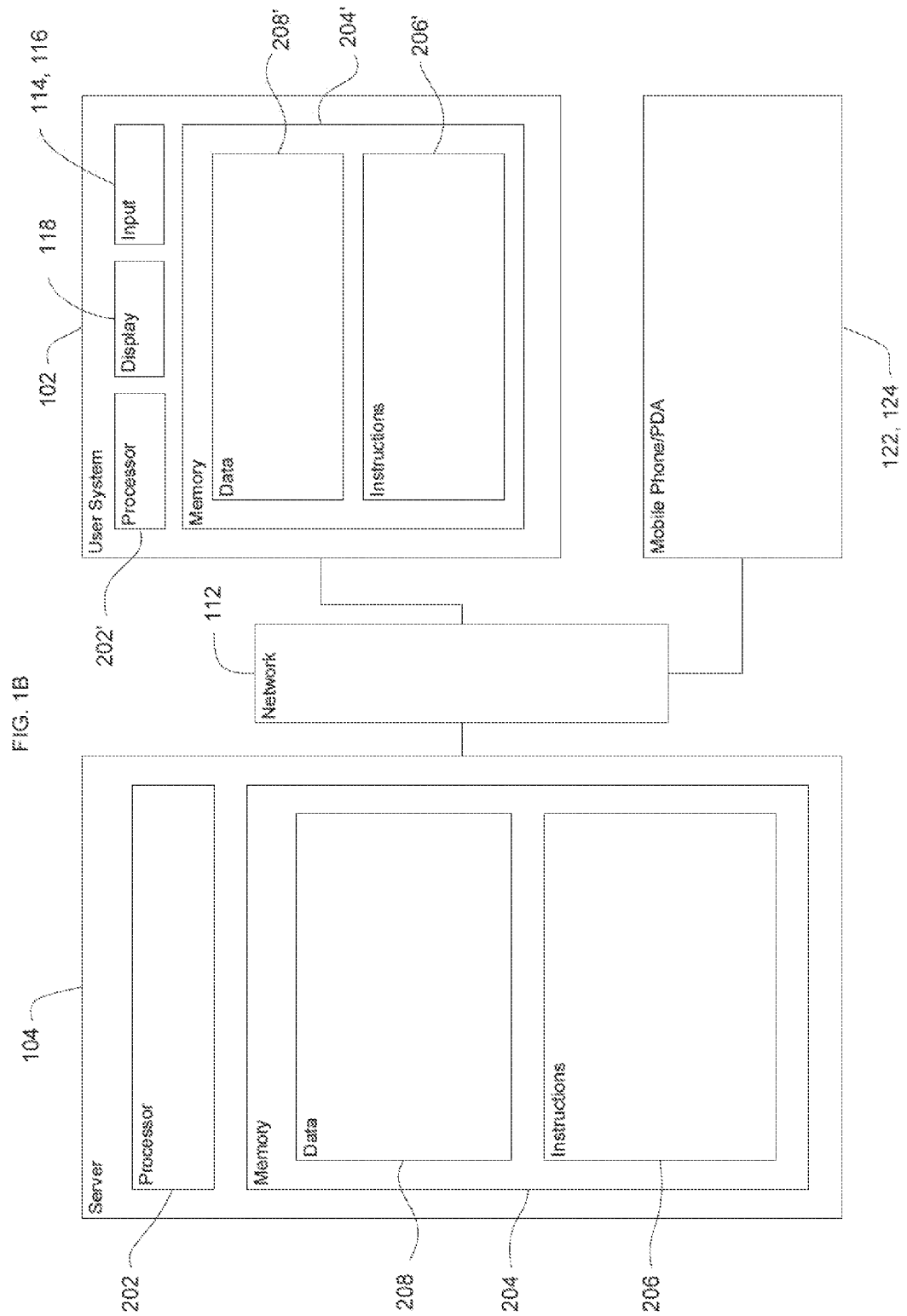

CT/MRI

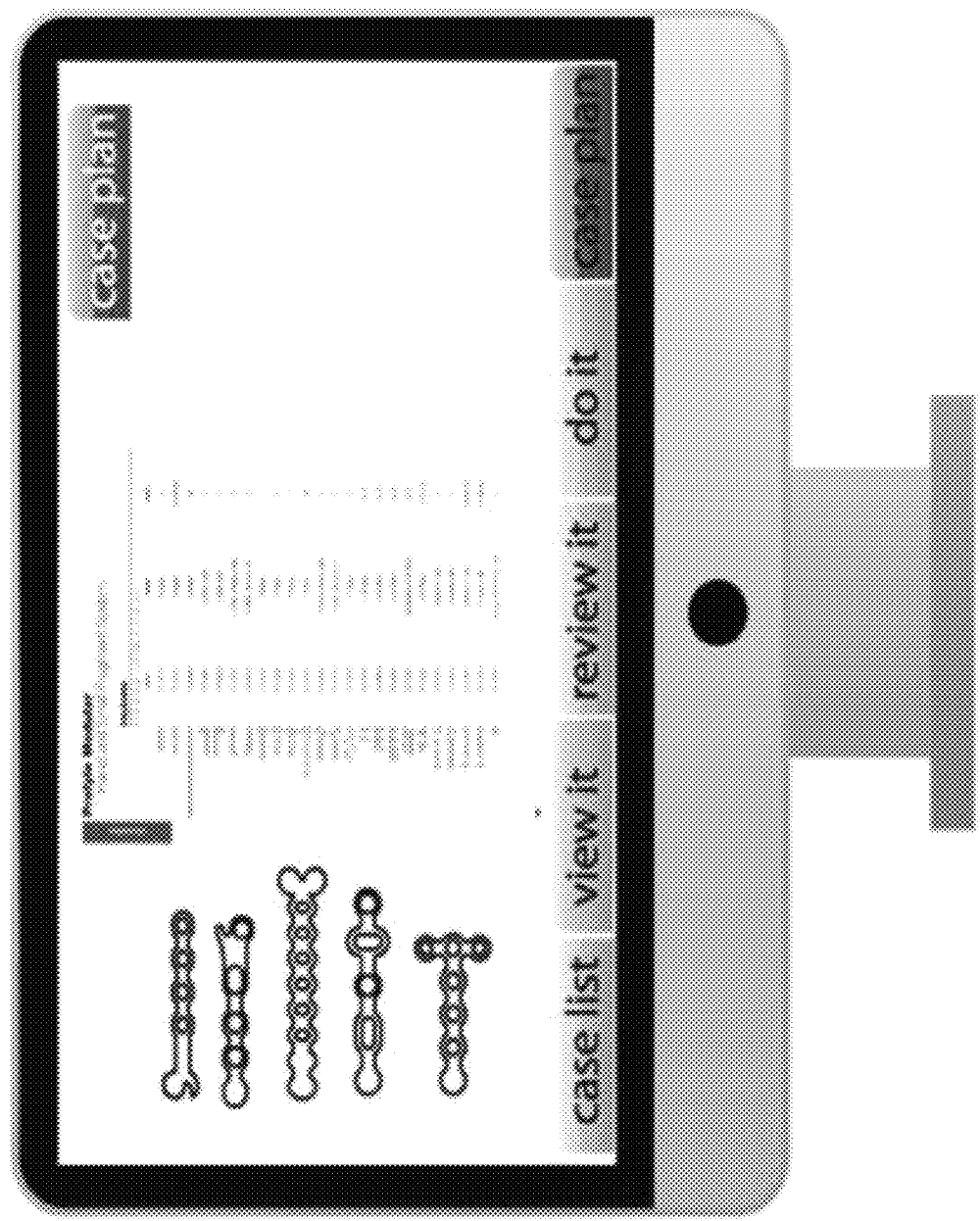

SURGICAL CASE PLANNING PLATFORM

CROSS-REFERENCE TO RELATED APPLICATIONS

This application claims the benefit of the filing date of U.S. Provisional Patent Application No. 61/479,950, filed Apr. 28, 2011, the disclosure of which is hereby incorporated herein by reference.

FIELD OF THE INVENTION

The present invention relates generally to a system for preoperatively planning a surgery, and in particular relates to using a reference library of medical devices and a plurality of previous surgical cases to generate a surgical case plan for correcting a surgical site of a patient.

BACKGROUND OF THE INVENTION

Generally, a diseased, injured or defective surgical site is repaired by a surgeon making intraoperative decisions during a surgery. The advent of preoperative planning has allowed a surgeon to make certain surgical decisions prior to conducting the actual surgery such as which implants or other surgical devices combined with operative technique/approach could be used to achieve a desired surgical outcome. The ability to view images or models of a patient's surgical site prior to surgery allows the surgeon to develop a plan of action for conducting the actual surgery.

BRIEF SUMMARY OF THE INVENTION

Surgeons may desire to have at their disposal as much relevant medical data as possible to improve the preoperative planning of surgeries. Particularly, surgeons should have access to as much useful and relevant information as practically available during the preoperative planning process. Such information should not only be gathered and analyzed from the patient that the surgery is being planned for, but also from other patients who have had a similar diseased, injured or defective surgical site.

A first aspect of the present invention is a system for preoperatively planning a present surgical case including a surgical site of a body of a patient. The system preferably includes a processing device and a modeling module managed by the processing device for producing a two or three-dimensional model of the present surgical case from at least one image taken of the surgical site of the body. The three-dimensional model is preferably manipulated for presentation on a display means as a corrected model representing the surgical site of the body of the patient.

According to one embodiment of the first aspect of the present invention, the system preferably further includes a database operatively coupled to the processing device and the modeling module. The database preferably includes a library of medical devices suitable to correct the surgical site of the body based on the corrected model. The database preferably further includes a separate library housing a plurality of previous surgical cases and case information configured for use in the preoperative planning of the present surgical case. Preferably, the processing device is configured to identify, retrieve and arrange at least one of the medical devices and at least one of the plurality of previous surgical cases for presentation on the display means as part of preoperatively planning the present surgical case. A surgical case plan is preferably generated from the aforementioned system such that the surgeon has a plan that he or she can consult during the actual surgery.

According to another embodiment of the first aspect of the present invention, the processing device is further configured to correlate similar surgical cases to a type of injury that the surgical site of the body is classified as.

According to yet another embodiment of the first aspect of the present invention, the plurality of previous surgical cases available for review are stored as separate three-dimensional models.

According to still yet another embodiment of the first aspect of the present invention, the processing device is further configured to select one of the separate three-dimensional models as being most similar to the three-dimensional model of the present surgical case.

According to still yet another embodiment of the first aspect of the present invention, the surgical site of the body of the patient includes a femur and the at least one medical device is a bone plate.

According to still yet another embodiment of the first aspect of the present invention, the corrected model comprises first and second corrected models. A first medical device of the library of medical devices is displayable on the display means as being engaged to the first corrected model and a second medical device of the library of medical devices is displayable on the display means as being engaged to the second corrected model.

A second aspect of the present invention is a computer-implemented method of preoperatively planning a present surgical case including a surgical site located on a portion of a body of a patient. The computer-implemented method preferably includes uploading, into a computer database stored in a cloud, at least one image taken of the surgical site of the body of the patient. The at least one image is preferably converted into a three-dimensional model displayable on a display means. The three-dimensional model is preferably manipulated such that the three-dimensional model is displayable on the display means as a corrected model representing a corrected surgical site. The method further includes providing, with a processor, at least one medical device from a library of medical devices stored in a device database, the at least one medical device being selectable in order to correct the surgical site of the body based on the corrected model. The method preferably further includes providing a plurality of previous surgical cases maintained in a case database, wherein the plurality of previous surgical cases is available for preoperatively planning the present surgical case.

According to one embodiment of the second aspect of the present invention, the method further includes categorizing the surgical site of the body as a type of injury and correlating similar surgical cases selected from the plurality of previous surgical cases to the type of injury.

According to another embodiment of the second aspect of the present invention, the plurality of previous surgical cases available for review are stored as separate three-dimensional models.

According to yet another embodiment of the second aspect of the present invention, the method further includes selecting one of the separate three-dimensional models as being most similar to the three-dimensional model of the present surgical case.

According to still yet another embodiment of the second aspect of the present invention, the surgical site of the body of the patient includes a femur and the at least one medical device is a bone plate.

According to still yet another embodiment of the second aspect of the present invention, the corrected model comprises first and second corrected models. A first medical device of the library of medical devices is displayable on the display means as being engaged to the first corrected model and a second medical device of the library of medical devices is displayable on the display means as being engaged to the second corrected model.

According to still yet another embodiment of the second aspect of the present invention, the method further includes receiving a selection from a user as to whether the first medical device or the second medical device is usable in the present surgical case to correct the surgical site of the body.

BRIEF DESCRIPTION OF THE DRAWINGS

A more complete appreciation of the subject matter of the present invention and the various advantages thereof can be realized by reference to the following detailed description in which reference is made to the accompanying drawings.

FIG. 1A-B illustrate an exemplary network for use with aspects of the invention.

FIG. 11 illustrates an example of a screenshot of a display showing a surgical case plan that is generated in accordance with further aspects of the invention.

DETAILED DESCRIPTION

The aspects, features and advantages of the present invention will be appreciated when considered with reference to the following description of preferred embodiments and accompanying figures. The same reference numbers in different drawings may identify the same or similar elements. Furthermore, the following description does not limit the present invention; rather, the scope of the invention is defined by the appended claims and equivalents.

Figure 1A:
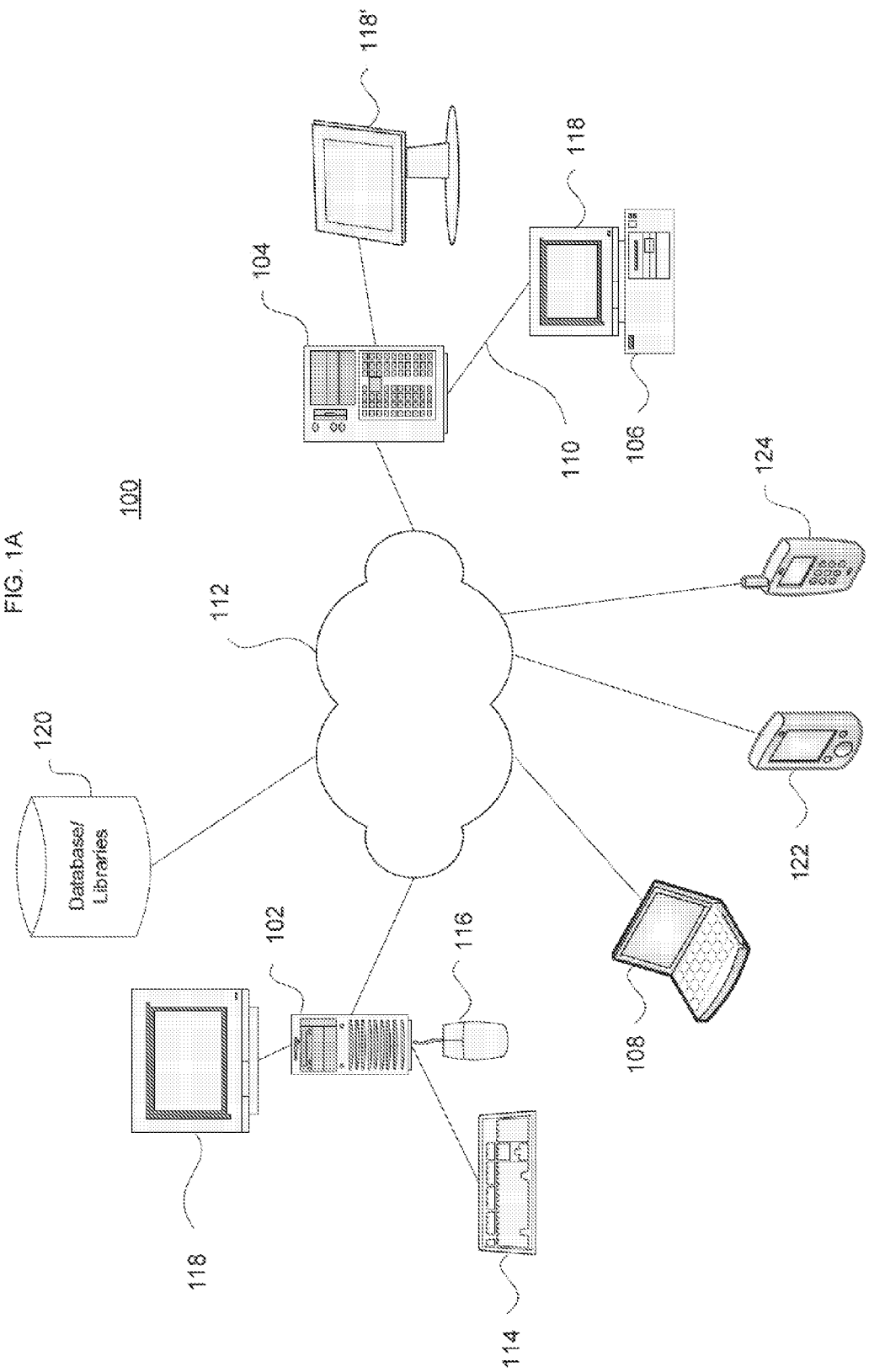

The case planning system discussed herein is very flexible and is suitable for use in many applications, including the preoperative planning of surgeries. An exemplary network architecture is illustrated in FIGS. 1A and 1B. FIG. 1A is a schematic diagram of a computer system depicting various computing devices that can be used alone or in a networked configuration in accordance with aspects of the invention. For example, this figure illustrates a computer network 100 that has a plurality of computers 102, 104 and 106, 108. The computers may be interconnected via a local/direct connection 110 or may be coupled via a communications network 112 such as a LAN, WAN, the Internet, etc. The network 112 may be a wired or wireless network.

Each computer processing system can include, for example, one or more computing devices having user inputs such as a keyboard 114 and mouse 116. Various other input devices may alternatively be used, such as pen-inputs, joysticks, buttons and, touch screens. The computers will typically also include a display 118, 118'. The display may be a CRT, LCD, plasma screen monitor, TV, projector, etc.

Each computer 102-108 may be a personal computer, server, etc. By way of example only, computers 102 and 106 may be personal computers while computer 104 may be a server and computer 108 may be a laptop, desktop, netbook or tablet PC. As shown in FIG. 1B, network 112 may include server 104 containing a processor 202, memory 204 and other components typically present in a computer.

Memory 204 is used to store information accessible by the processor 202, such as instructions 206 that may be executed by the processor 202 and data 208 that may be retrieved, manipulated or stored by the processor. The memory may be of any type capable of storing information accessible by the processor, such as a hard-drive, ROM, RAM, optical recording medium, flash drive, etc.

The processor 202 may be an off the shelf CPU from Intel Corporation or Advanced Micro Devices, for example. Alternatively, the processor 202 may be a dedicated controller for executing operations, such as an ASIC or programmable logic.

The instructions 206 may comprise any set of instructions to be executed directly or indirectly by the processor. The terms "instructions," "steps" and "programs" may be used interchangeably herein. The instructions may be stored in any computer language or format, such as in object code or modules of source code. The functions, methods and routines of instructions in accordance with aspects of the invention are explained in more detail below.

Data 208 may be retrieved, stored or modified by processor 202 in accordance with the instructions 206. The data may be stored as a collection of data, but is not limited by any particular data structure. By way of example only, the data may be stored in registers/RAM, in a relational database, as one or more XML documents, in an imagery-specific format, etc.

Although the processor 202 and memory 204 are functionally illustrated in FIG. 1B as being within the same block, the processor and memory may actually comprise multiple processors and memories that may or may not be stored within the same physical housing or location. For example, some or all of the instructions or data may be stored on a removable Blu-ray disc and others within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 204 such as hard drives or the like. For instance, server 104 may be coupled to storage device 120 (FIG. 1A) that maintains one or more databases and/or libraries. The storage device 120 may comprise a server farm or cloud computing system having a storage capacity for large amounts of data (e.g., terabytes).

Each client computer or user system 102 may be configured similarly to the server 104, with a processor 202', memory 204', instructions 206' and data 208', as well as one or more user input devices 114, 116 and a user output device, such as display 118. Each client computer may be a general purpose computer, intended for use by a person, having all the components normally found in a personal computer such as a central processing unit (CPU), display, hard-drive, mouse, keyboard, touch-sensitive screen, speakers, microphone, modem and/or router and all of the components used for connecting these elements to one another.

Although only a few computers are depicted in FIGS. 1A and 1B, it should be appreciated that a typical system can include a large number of connected servers and clients, with each different computer being at a different node of the network.

Communication across the network, including any intervening nodes, may be facilitated by any device capable of transmitting data to and from other computers, such as modems, network interfaces and wireless interfaces. Server 104 may be an application server, such as a load-balanced web server system.

Moreover, computers in accordance with the systems and methods described herein may comprise any device capable of processing instructions and transmitting data to and from humans and other computers, including network computers lacking local storage capability, PDA's 122 with modems and Internet-capable wireless phones 124.

Figure 2:
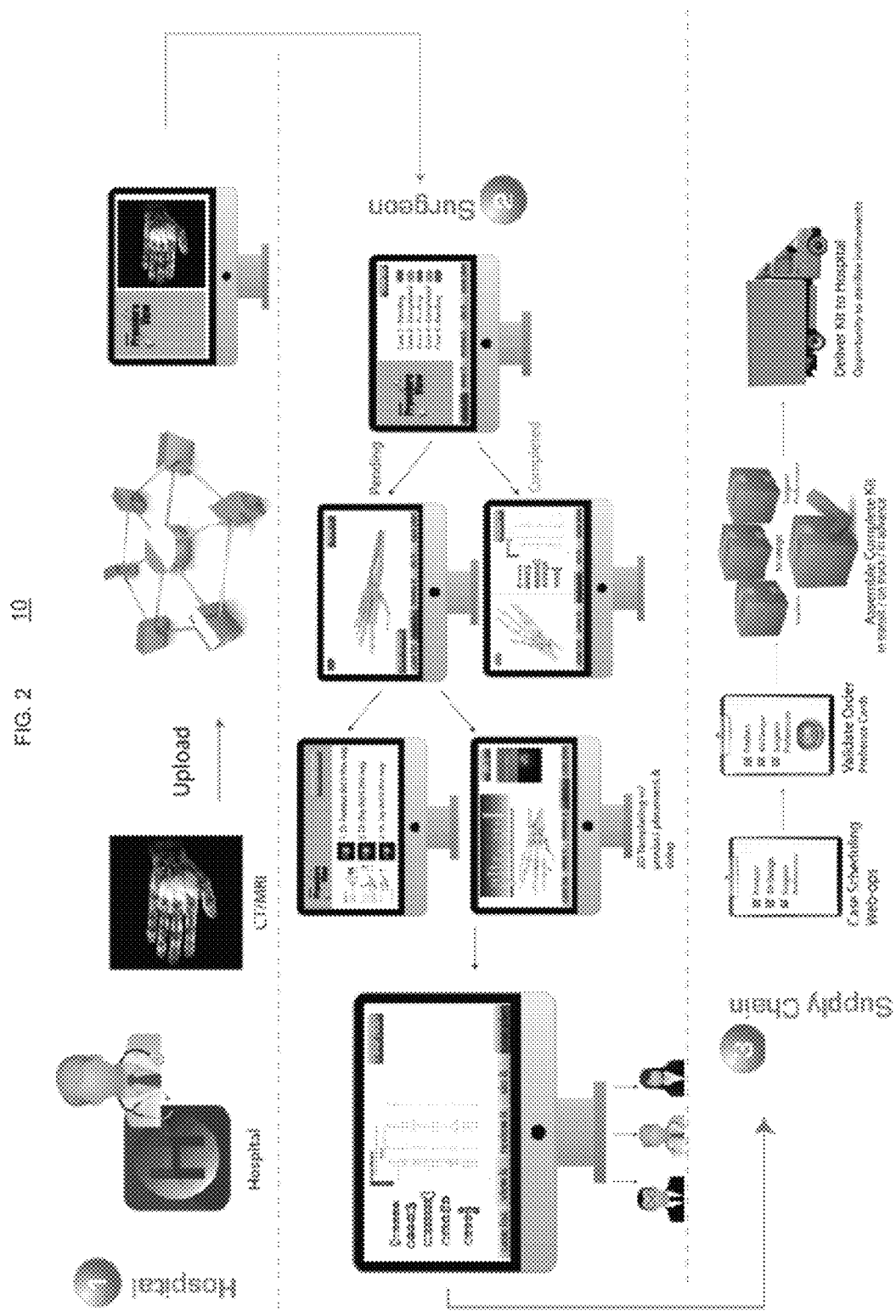
FIG. 2 illustrates a procedure overview in accordance with one embodiment of the invention.

FIG. 2 presents a case planning system in accordance with aspects of the invention. The case planning system is designated generally by reference numeral 10. As shown in those figures, system 10 includes several screenshots depicting examples of what a technician and/or surgeon may see during the preoperative planning process. Generally, system 10 includes the various computing devices shown in FIGS. 1A-B. For instance, as described herein, a server such as server 104 may maintain one or more databases or libraries, which may be maintained by storage device 120, accessible via network 112. Different users, such as surgeons, laboratory technicians, nurses, scientists and others, may access some or all of the databases/libraries via different client devices, including computers 102, 106 and 108, as well as PDA 122 and mobile phone 124.

Figure 3:
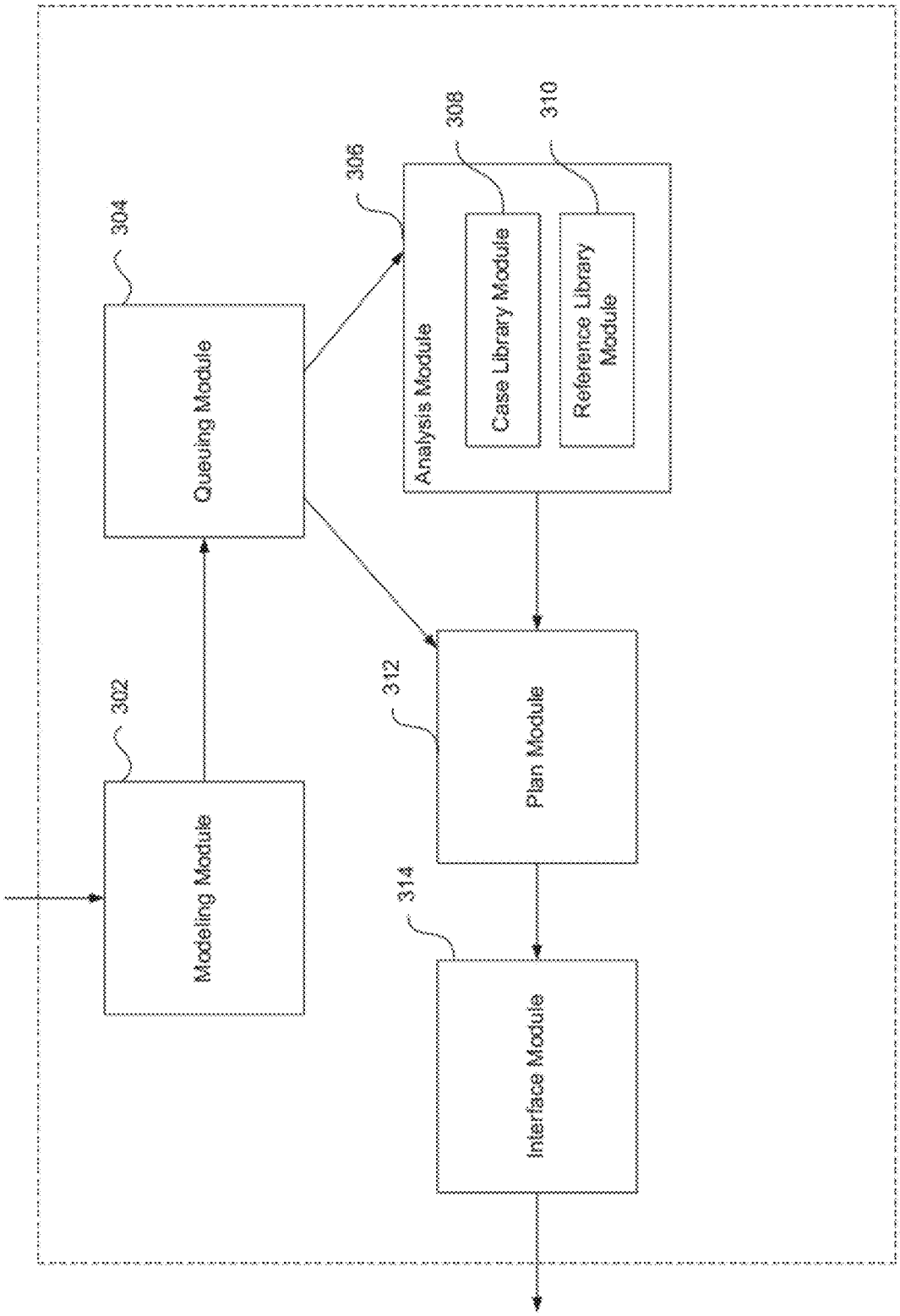
FIG. 3 illustrates a system in accordance with aspects of the invention.

FIG. 3 presents an exemplary system 300 illustrating functional modules in accordance with aspects of the invention. As shown, the functional modules may include a modeling module 302, a queuing module 304, an analysis module 306, a plan module 312 and an interface module 314. As shown in FIG. 3, the analysis module may include a case library sub-module 308 and a reference library sub-module 310. The modules may be implemented in software and/or hardware and may be distributed among one or more of the computers 202, 204, 206 and 208 of FIG. 1A.

System 300 includes a processing device (such as processor 202) and a modeling module 302 managed by the processing device. The modeling module produces a three-dimensional model of the present surgical case from at least one image taken of the surgical site of the body. The at least one image may include CAT scans, PET scans, MRI images, X-rays, sonograms or other such images taken by known medical imaging techniques. Individual images may be two-dimensional images that may be processed to obtain a three-dimensional image.

Once completed, the models enter queuing module 304. Each model represents a case and the cases are stored in the queuing module as either "pending" or "completed." Pending cases enter analysis module 306 in which previous surgical cases and reference libraries of medical devices are present for the preoperative planning of the surgery. Upon completion of the analysis module 306, a surgical case plan is generated as depicted by plan module 312.

As shown in FIG. 3, the modeling module 302 may receive input from external sources, and the interface module 314 may output processed results. In one example, the modules 304, 306 and 312 may operate as part of a run-time environment, while the modules 302 and 314 may operate in an off-line mode, although such operation is not required.

Figure 4:
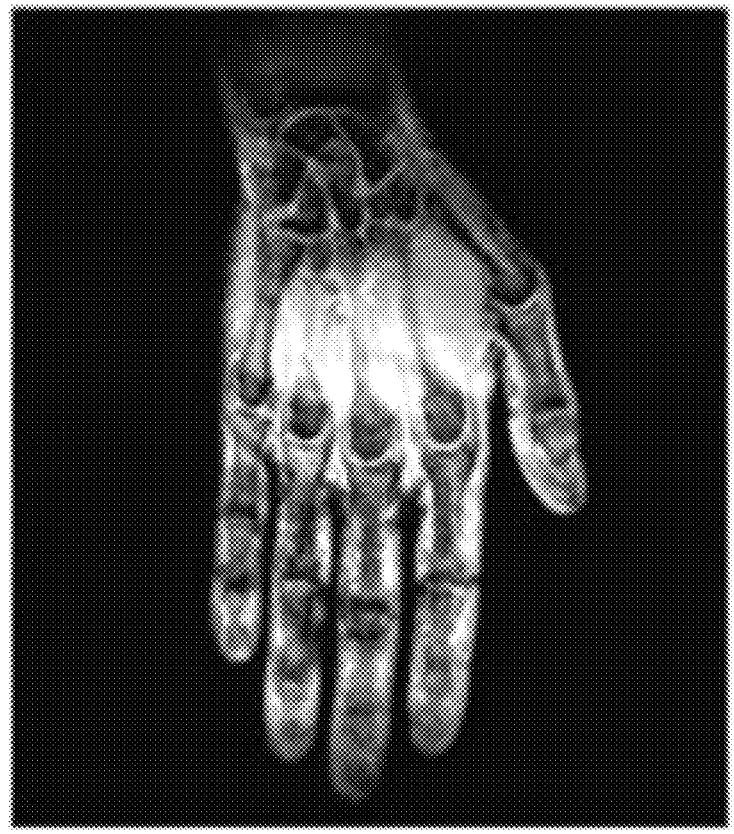
FIG. 4 illustrates an exemplary CT/MRI image slice of a diseased, injured or defective surgical site of a patient.

A system according to one embodiment is preferably used for correcting fractures of the knee, ankle or wrist, but can be used for correcting any type of bone fracture in the human body. Further, the system may be used for joint reconstruction, sports medicine, spine injuries, and craniomaxillofacial applications, for example. The system may also be used by veterinarians for the preoperative planning of surgeries on animals. In the present example, the system is used to preoperative plan a surgery that will be performed on a patient having a diseased, injured or defective portion or surgical site on his or her body. In order for a surgeon to preoperatively plan how the surgical site should be corrected, the site must first be imaged. Here, the system may use x-ray images, but preferably, computed tomography ("CT") or magnetic resonance imaging ("MRI") is used to obtain images of the patient's surgical site as shown in FIG. 4.

In the case of CT or MRI, the surgical site is scanned such that a plurality of image slices are preferably generated from the scan. These images generated from the scan are then uploaded, using a picture archiving and communication system ("PACS") station, to a storage system. The storage system may be storage device 120, for example, as shown in FIG. 1A. The storage device 120 may comprise a "cloud" database in which data is maintained in a distributed architecture. Once the images are uploaded to the cloud, the images can be stored and transmitted to servers, computers, and the like.

Figure 5:
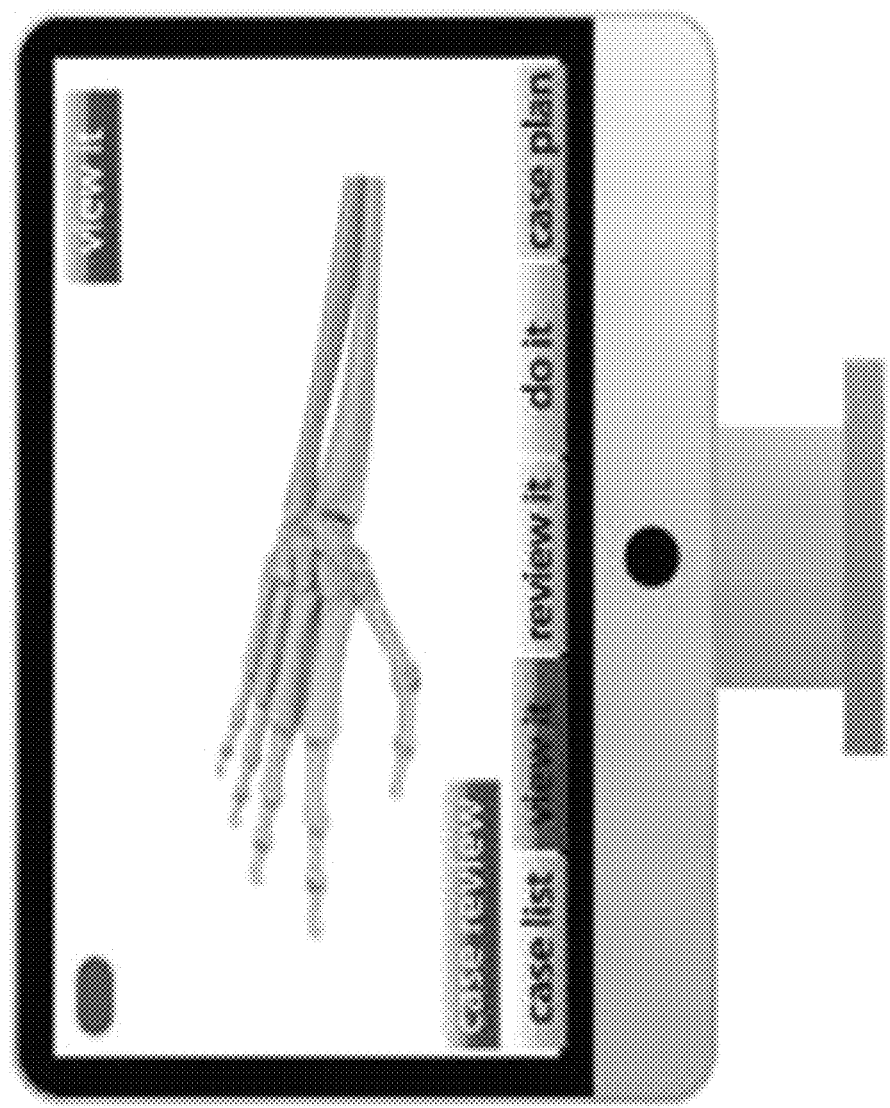
FIG. 5 illustrates an exemplary model of the position and orientation of bones located at the diseased, injured, or defective surgical site of the patient.

In one embodiment, the method further includes the creation of one or more three-dimensional ("3D") models of the surgical site from the CT or MRI image data as shown in FIG. 5. A technician can create the one or more models by any known modeling technique and with any known modeling software. Preferably, the one or more models are created using an auto segmentation process.

Figure 6:
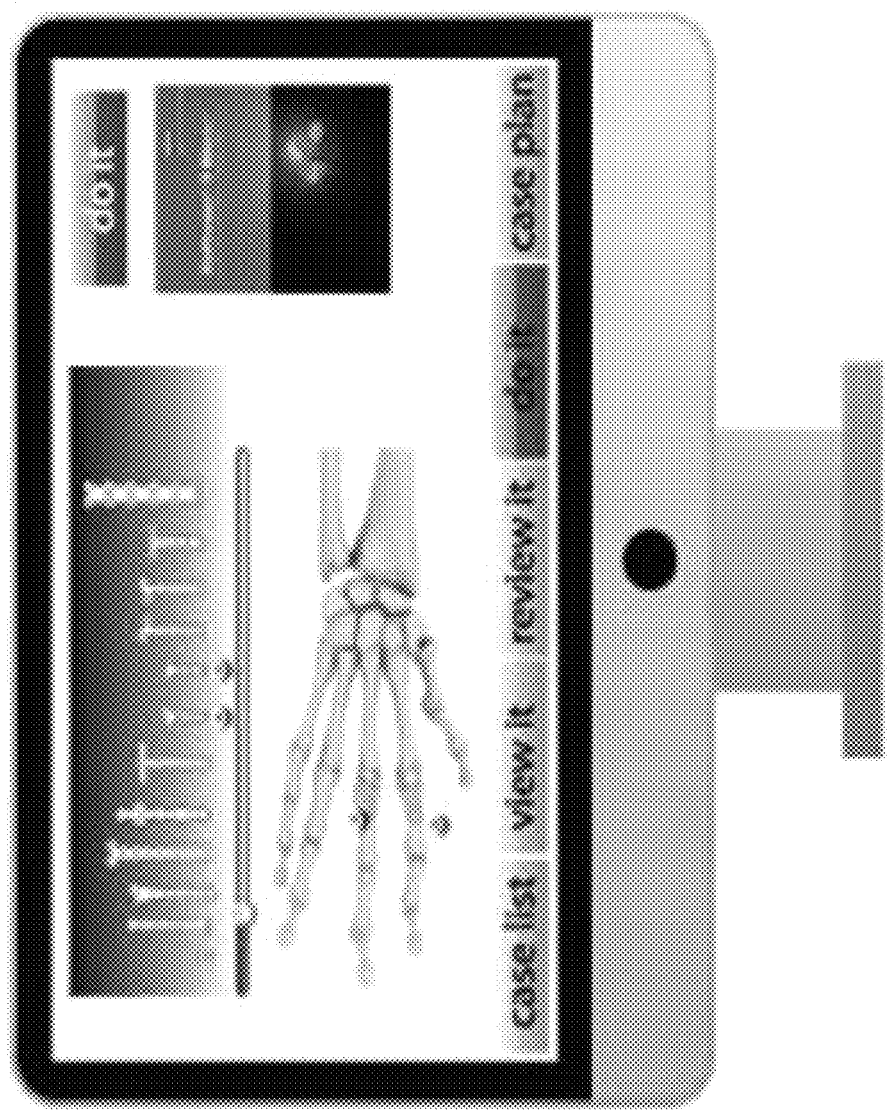
FIG. 6 illustrates the exemplary bone model of FIG. 5 shown in a corrected position, including examples of medical devices contained in a library that can be applied to the bone model.

Once the one or more models are created, the models are manipulated to approximate the position of bones, for example, prior to any disease or injury having occurred as shown in FIG. 6. In the case of a defect present at birth, the models are manipulated such that the bones are positioned with respect to one another in the approximate location as they would have been but for the birth defect having occurred. While the present example contemplates software that can be used to automatically manipulate the models based on certain parameters, the surgeon can manipulate the models such that the bones become arranged in a desired or corrected position based on his or her skill and expertise, including knowledge of human anatomy.

In the case of the surgical site being the knee joint, for example, the distal femur and proximal tibia would at least be imaged in order to create models of these portions of the femur and tibia. Once the models are created, the current varus or valgus angle of the knee joint can be determined and the model can be manipulated to correct any misalignment based on the anatomical or mechanical axes, for example. As stated above, the method of the present invention can be used for any type of fracture of bone or bones in the human body, and thus, the knee joint is just one example of a portion of a patient's body that can be corrected using the method of the present invention.

The one or more bone models can preferably be rotated in any plane, viewed at an angle, and zoomed in and out, for example. Once the bone models are manipulated to correct the fracture, the surgeon will be presented with several options to preoperatively plan the surgery. This is also considered as managing the present case. Examples of the options to manage the case include, for example, access to: 1) a case library; 2) a "fix it" feature; and 3) a case plan.

A first option of the surgeon, when selected, is the case library option which will present the surgeon with the following three content choices: 1) a decision tree; 2) case review; and 3) surgical approaches.

Figure 8:
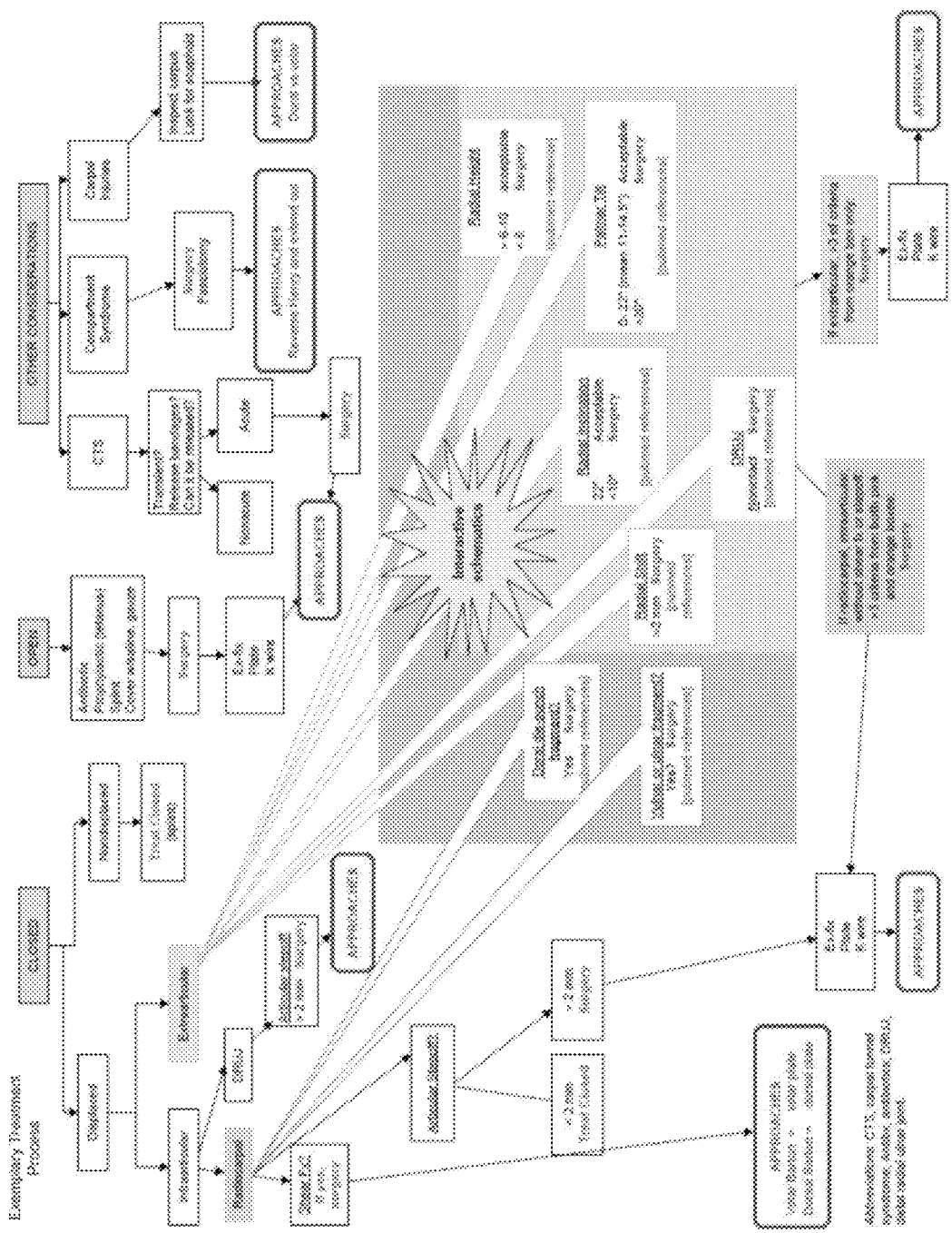
FIG. 8 illustrates an example of one type of treatment process in accordance with one embodiment of the invention.
Figure 9:
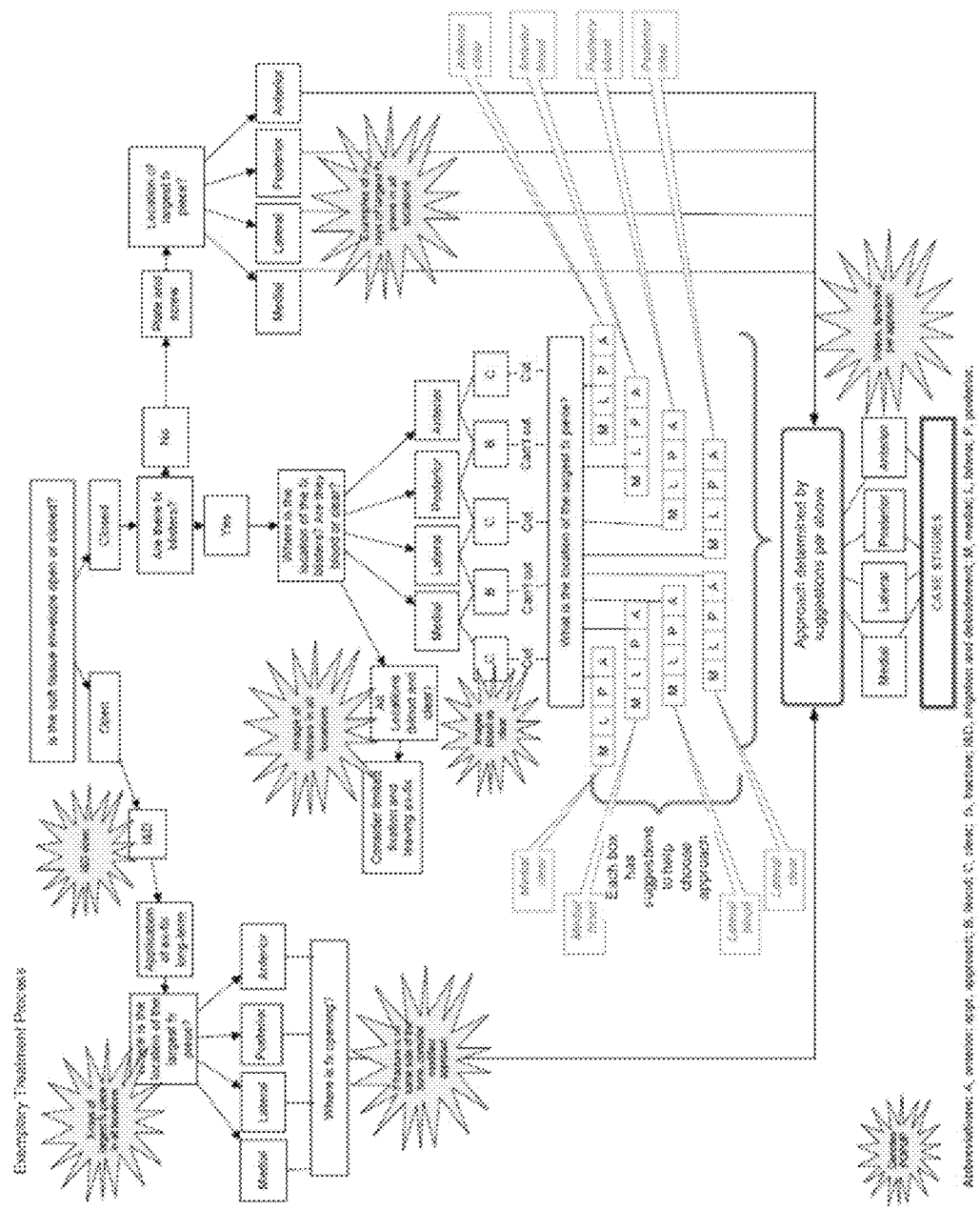
FIG. 9 illustrates an example of another type of treatment process in accordance with another embodiment of the invention.

The first of the three content choices is decision tree which is a process-based approach to manage the fracture as shown in FIGS. 8 and 9, for example. The decision tree is an algorithmic representation of orthopedic scenarios that offer treatment considerations based on presentation and related symptoms. This includes interactive elements that may be presented in a question/answer scenario and may include video presentations.

The second of the three content choices is the case review, which allows the surgeon to sample best practice examples of actual cases or preconfigured case scenarios demonstrating how industry leading surgeons have handled or would handle similar cases. Case review of actual orthopedic surgical cases may include many elements. For example, case review may include what is considered as the case history of a particular patient, including: 1) age, sex, chief complaint, history of injury. Relevant medical history may also be included such as vital signs, lab results, whether the patient has any underlying health issues such as diabetes or cardiovascular disease, for example, and whether there is a history of drug and/or alcohol use, and other medical history that may or may not be relevant to the current case. Case review may also include examinations of the patient, including physical findings and relevant systems examination. Studies may also be included such as x-rays, CT scans, MRI scans, 3D views, and other studies. Diagnosis may also be included such as specific diagnosis and differential diagnoses to consider. Further, treatment and management plans may also be included such as surgical solution, technique tips, postoperative studies (CT/MRI, x-rays, and 3D views, for example), postoperative management, other possible surgical solutions and approaches, case discussions, and references. It is also contemplated that surgeons can add cases that they themselves are working on or have worked into the case review option.

The third of the three content choices included in the case library is what is referred to as surgical approaches. This desirably includes a video review including demonstrations of possible scenarios for the specific type of fracture.

A second option of the surgeon, when selected, is the "fix it" option which will provide him or her with several options to manage the disease, condition, or for example, fracture. One option of the surgeon is to reduce the fracture if appropriate. Another option is to apply an appropriate product, such as plates and screws, for example, to the bones to stabilize the fracture. A build list of all the components used will be maintained, including description and catalog number of each component. The build list may be maintained in a separate database and stored in storage device 120.

A third option of the surgeon, when selected, is the case plan option which will allow the surgeon to generate a patient specific case plan that includes: 1) images of the bone structure as manipulated by the surgeon showing product placement; 2) bill of materials for all components to be used in the case; and 3) summary of approach to be used. Preferably, the surgeon will be able to download and view their case plan to their PDA or other portable device using an application viewer.

In another embodiment, the surgeon has at least the following three choices in generating a surgical case plan for correcting the injury: 1) a library of medical devices; 2) a library of previous surgical case files; and 3) an auto correct feature where a surgical case plan is generated via certain parameters defined in an algorithm.

Prior to using either the library of medical devices or library of previous surgical cases, the surgeon or system itself may characterize the surgical site being preoperatively planned as a type of injury. The reason that a type of injury would be defined is to provide the surgeon with the most relevant information available in the system. For instance, in a case where the surgical site is a wrist fracture, implants and medical devices that are known to correct distal radius fractures, for example, would be readily available. Also, all previous surgical cases of distal radius fractures contained in the system are also readily available for review. By readily available, such information is uploaded to be viewed on the same or a different display means configured to display the aforementioned models of the surgical site.

Once the type of injury is defined, in the case of the library of medical devices, such medical devices known to correct certain fractures are uploaded as also shown in FIG. 6. In one embodiment, a icon will be present on a display means that when selected would display a plurality of implants and medical devices, such as fracture plates, screws, pins, wires, connectors, and the like, for example. Because the type of injury is defined, the correct sizes of medical devices are present for selection. The surgeon has the ability to select any of the medical devices available for the type of injury, and once selected, the medical device is applied to the models in a position that would stabilize and fix the fracture.

The surgeon has the ability to move the medical device or devices applied to the surgical site in a plurality of different positions. Fixation means, such as screws, could be added to fracture plates to see how the screws would be positioned in the bone during the actual surgery. The surgeon has the further ability to pick and choose the available medical devices through a trial and error approach. Medical devices that are chosen to be applied to the models can be deleted and replaced with other available medical devices until the surgeon is satisfied that the medical devices applied to the models are sufficient or optimal for correcting the surgical site.

Figure 7:
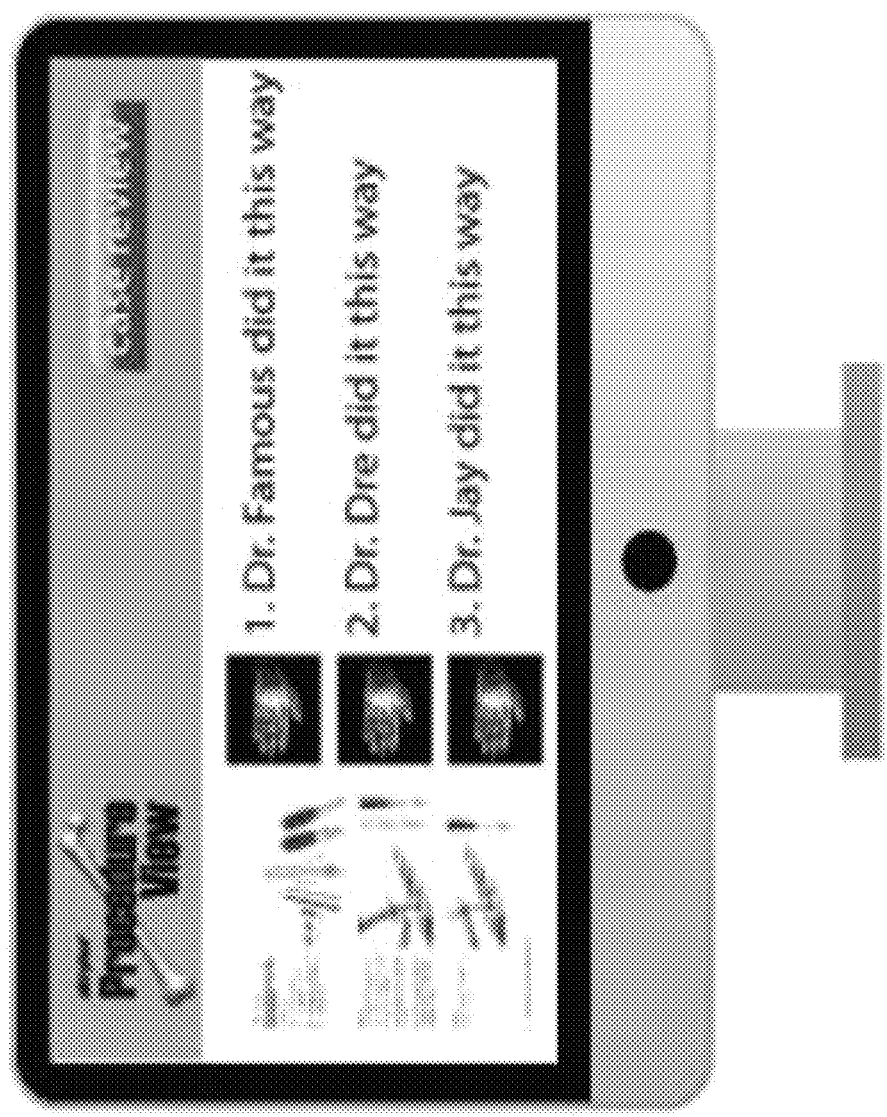
FIG. 7 illustrates an example of a screenshot of a display showing a library of previous related surgical cases.

Also available to the surgeon in the preoperative planning process is a library of surgical case files as shown in FIG. 7. Once the type of injury is defined, such surgical cases files related to the type of injury are retrieved. In one embodiment, an icon will be present on a display means that when selected would display a plurality of surgical case files. Each surgical case file available for review includes relevant information that can be used by the surgeon to preoperatively plan the surgery. For example, a surgical case file may include photographs, doctor records, patient history information, and all images taken of the surgical site such as x-ray, CT and MRI images. Each surgical case file may not include exactly the same type of information. The information available to the surgeon is whatever information included in the file or whatever information has been cleared for use and not subject to patient privacy laws.

The surgeon has the ability to select any of the previous surgical case files available for the type of injury defined, and once selected, the surgeon can review the file to see what medical devices were used in that case so that those medical devices can be selected from the library and applied to the models in a position that would stabilize and fix the fracture. The surgeon then has the ability to move the medical device or devices applied to the surgical site in a plurality of different positions. Fixation means, such as screws could be added to fracture plates to see how the screws would be positioned in the bone during the actual surgery. The surgeon has the further ability to review additional previous surgical cases and pick and choose the available medical devices through a trial and error approach. Medical devices that are chosen to be applied to the models can be deleted and replaced with other available medical devices until the surgeon is satisfied that the medical devices applied to the models are sufficient or optimal for correcting the surgical site.

As shown in FIGS. 8 and 9, for example, the decision tree is an algorithm-based approach to managing the fracture at the surgical site. These algorithms are merely exemplary for specific types of injuries at specific surgical locations. As shown in FIG. 8, the flowchart shown is one type of algorithm-based approach for a distal radius fracture. This is an exemplary approach that the surgeon can deviate from based on his or her own decisions and knowledge in this area.

As shown, the process breaks into certain considerations based on whether the surgical site is closed or open. Open surgical sites (e.g., compound fractures) have certain surgical protocols that are different than closed surgical sites. For instance, antibiotic, tetanus shots, and splints are generally applied to the injured area prior to surgery being performed. In many cases, the surgery includes the addition of external fixation frames, plates and/or k-wires. In contrast, closed surgical sites offer a different set of considerations. Different approaches are considered on whether the fracture is nondisplaced or displaced. Nondisplaced fractures are generally treated with splints and the soft tissue surrounding the surgical site is therefore not accessed by the surgeon in a surgical procedure. Different approaches are considered in the case of a displaced fracture. A certain set of decisions are made if the fracture occurs outside the joint (extraarticular) or the fracture goes into the joint (intraarticular). The process may include several other considerations shown in FIG. 8 prior to the surgical case plan being generated.

Figure 10:
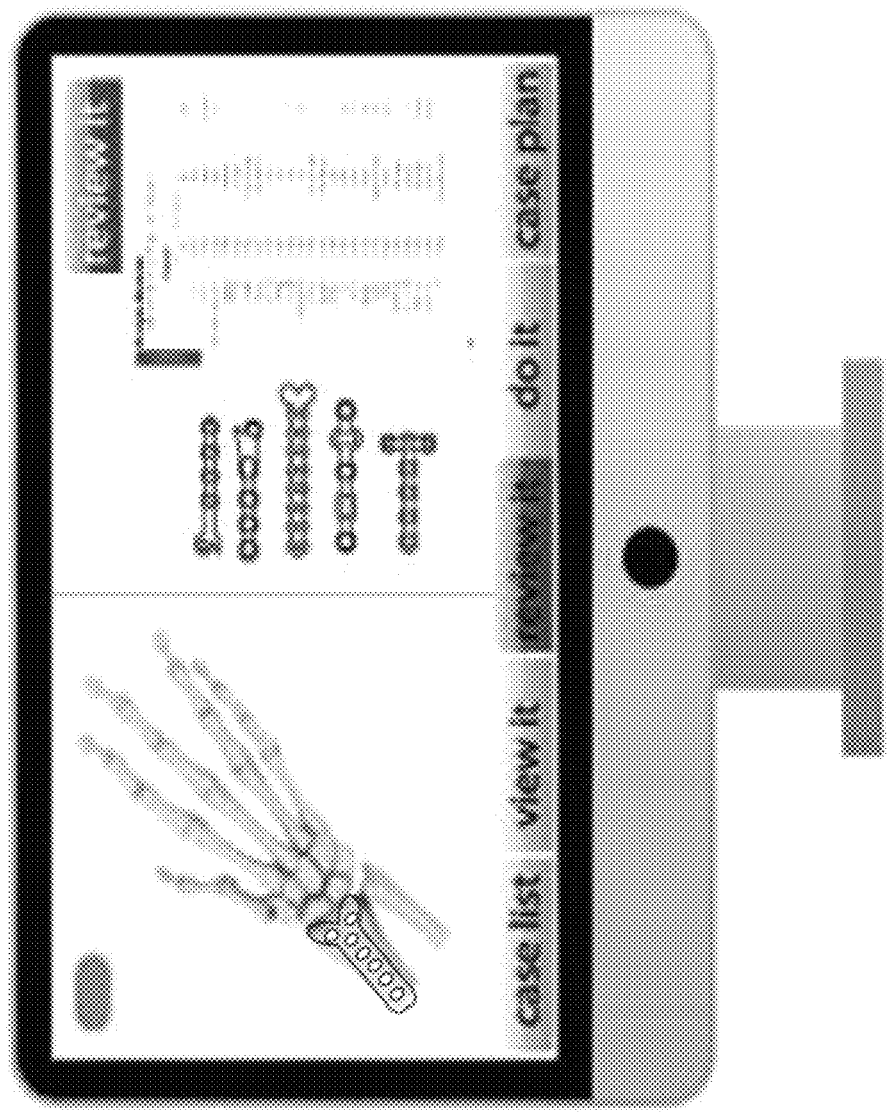
FIG. 10 illustrates an example of a completed case plan showing a medical device or devices implanted in a particular position on the bones included in the surgical site in accordance with aspects of the invention.

After the surgeon is satisfied that he or she has corrected the fracture with the appropriate medical devices available in the system, a completed case plan is shown. FIG. 10 illustrates a completed case plan showing a medical device or devices implanted in a particular position on the bones included in the surgical site.

From this case plan, a surgical case plan is generated as shown in FIG. 11. The surgical case plan generated includes all the instructions necessary for the surgeon to perform the actual surgery. For example, the surgical case plan includes all the medical devices selected for the surgery with instructions for device location and orientation. The surgical case plan may also include the alignment instruments needed to set the medical devices in place as well as instructions for drill depth for preparing screw holes for receiving fixation screws, for example.

As discussed above, aspects of the technology may include medical histories or other patient-related data. Such personal information should be maintained in a database(s) that complies with all applicable regulations and guidelines. The data may be stored in encrypted form so that only authorized users may access it.

The system may also have inventory capabilities such that once a medical device or devices are included as part of the generated case plan and sent to the surgeon for surgery, the system may send out an order to replace the medical device or devices. The surgeon may also be able to order medical devices to add to the system or replace certain medical devices in the system with others. The medical devices in the system may also be linked to the supply chain such that the location of a medical device is known whether it be with a manufacturer, supplier, or distributor, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A computer-implemented method of preoperatively planning a present surgical case including a surgical site located on a portion of a body of a patient, the method comprising:
uploading, into a computer database, at least one image taken of the surgical site of the body of the patient;
converting the at least one image into a three-dimensional model displayable on a display means;
manipulating the three-dimensional model such that the three-dimensional model is displayable on the display means as a corrected model representing a corrected surgical site;
providing, with a processor, at least one medical device from a library of medical devices stored in a device database, the at least one medical device being selectable in order to correct the surgical site of the body based on the corrected model; and
providing a plurality of previous surgical cases maintained in a case database the plurality of previous surgical cases being made available for preoperatively planning the present surgical case,
wherein the surgical site of the body of the patient includes a femur and the at least one medical device is a bone plate.

2. The method of claim 1, further comprising categorizing the surgical site of the body as a type of injury.

3. The method of claim 2, further comprising correlating similar surgical cases selected from the plurality of previous surgical cases to the type of injury.

4. The method of claim 1, wherein the plurality of previous surgical cases available for review are stored as separate three-dimensional models.

5. The method of claim 4, further comprising selecting one of the separate three-dimensional models as being most similar to the three-dimensional model of the present surgical case.

6. The method of claim 1, wherein:
the corrected model comprises first and second corrected models;
a first medical device of the library of medical devices is displayable on the display means as being engaged to the first corrected model; and
a second medical device of the library of medical devices is displayable on the display means as being engaged to the second corrected model.

7. The method of claim 6, further including receiving a selection from a user as to whether the first medical device or the second medical device is usable in the present surgical case to correct the surgical site of the body.

8. A system for preoperatively planning a present surgical case including a surgical site of a body of a patient, comprising:
- a processing device;
- a modeling module managed by the processing device for producing a three-dimensional model of the present surgical case from at least one image taken of the surgical site of the body, the three-dimensional model being configured for manipulation for presentation on display means as a corrected model representing the surgical site of the body of the patient; and
- a database operatively coupled to the processing device and the modeling module, the database comprising:
  - a library of medical devices suitable to correct the surgical site of the body based on the corrected model; and
  - a plurality of previous surgical cases configured for use in the preoperative planning of the present surgical case;
- wherein the processing device is configured to arrange at least one of the medical devices and at least one of the plurality of previous surgical cases for presentation on the display means as part of preoperatively planning the present surgical case, and
- wherein the surgical site of the body of the patient includes a femur and the at least one medical device is a bone plate.

9. The system of claim 8, wherein the processing device is further configured to correlate similar surgical cases to a type of injury that the surgical site of the body is classified as.

10. The system of claim 8, wherein the plurality of previous surgical cases available for review are stored as separate three-dimensional models.

11. The system of claim 10, wherein the processing device is further configured to select one of the separate three-dimensional models as being most similar to the three-dimensional model of the present surgical case.

12. The system of claim 8, wherein:
- the corrected model comprises first and second corrected models;
- a first medical device of the library of medical devices is displayable on the display means as being engaged to the first corrected model; and
- a second medical device of the library of medical devices is displayable on the display means as being engaged to the second corrected model.

* * * * *